United States Patent [19]

Rheinberger et al.

[11] Patent Number: 5,539,017
[45] Date of Patent: Jul. 23, 1996

[54] USE OF A THERMALLY CURABLE COMPOSITION AS DENTAL MATERIAL

[75] Inventors: Volker Rheinberger, Vaduz; Norbert Moszner, Eschen, both of Liechtenstein

[73] Assignee: Ivoclar AG, Liechtenstein

[21] Appl. No.: 376,935

[22] Filed: Jan. 23, 1995

[30] Foreign Application Priority Data

Jan. 26, 1994 [DE] Germany .......................... 44 02 766.4

[51] Int. Cl.⁶ .................. C08G 2/26; C08G 16/00; C08G 67/00; C08K 5/17
[52] U.S. Cl. .................. 523/116; 523/115; 523/118; 524/542; 525/471; 525/539; 528/224
[58] Field of Search ..................... 523/115, 116, 523/118; 525/471, 539; 528/224; 524/542

[56] References Cited

U.S. PATENT DOCUMENTS

| | | | |
|---|---|---|---|
| 3,346,620 | 10/1967 | Siggins et al. | 560/112 |
| 3,361,700 | 1/1968 | Archer et al. | 524/288 |
| 5,017,649 | 5/1991 | Clemens | 525/59 |
| 5,227,413 | 7/1993 | Mitra | 523/116 |

FOREIGN PATENT DOCUMENTS 1492183  9/1964  Germany .

*Primary Examiner*—Paul R. Michl
*Assistant Examiner*—Andrew E. C. Merriam
*Attorney, Agent, or Firm*—Nixon, Hargrave, Devans & Doyle

[57] ABSTRACT

The use of a thermally curable composition as dental material or constituent of a dental material is described, which composition contains one or more β-dicarbonyl compounds and one or more α,β-unsaturated carboxylic acid esters, the curing of the composition taking place in the presence of a catalyst base.

17 Claims, No Drawings

USE OF A THERMALLY CURABLE COMPOSITION AS DENTAL MATERIAL

The invention relates to the use of a thermally curable composition as dental material or constituent of a dental material and to dental articles moulded therefrom.

The requirements which are to be met by compositions which are to be used as dental materials or constituents thereof are manifold and vary according to the type of dental material. An essential requirement to be met by all dental materials is that these are stable under the conditions prevailing in the oral cavity and do not hydrolyse in particular as a result of possible contact with saliva. In the case of curable dental materials, such as e.g. filling materials and polymer materials for the production of artificial teeth, particular importance is placed on the fact that there is only a slight volume shrinkage during the curing process. If there is too much volume shrinkage, then fitting inaccuracies of the cured material are an inevitable result. Curable dental materials which come into direct contact with foods in the oral cavity should further be characterized by a high hardness. Finally, it is moreover particularly desirable that the curing process can be carried out in a simple manner without the aid of expensive apparatus.

Polymers which cure in a simple manner, namely thermally at room temperature, are known. Vinyl monomers are the starting products for their manufacture. These are converted to the desired polymers by radical polymerisation with redox initiator systems, such as e.g. peroxide/amine combinations or with boron alkyls, by cationic polymerisation with acid catalysts, or by anionic polymerisation using group transfer catalysts (cf. Houben-Weyl: Methoden der anorganischen Chemie, Volume E 20, Part 1, pages 15, 94 and 153, Thieme-Verlag, Stuttgart 1986). The radical or cationic polymerisation can likewise be initiated using photoinitiators (cf. H. J. Timpe, H. Baumann, Photopolymere: Prinzipien und Anwendungen, Deutscher Verlag für Grundstoffindustrie, Leipzig 1988, pages 49 and 95).

It is a disadvantage with these known polymers that the polymerisation processes carried out in order to cure them are sensitive to the presence of e.g. oxygen and water. For example, radical polymerisation is severely inhibited by oxygen and anionic and cationic polymerisation by water or electrophilic and nucleophilic impurities respectively. Also, on carrying out a cross-linking polymerisation, a large volume shrinkage occurs, with the result that polymers deposited on a substrate have a tendency to rise and peel off from the substrate surface.

Other polymer materials which can be cured at room temperature are polyurethanes or polyureas which are produced by reacting diols or diamines with di- or multiisocyanates (cf. H.-G. Elias, Makromoleküle, Volume 2, page 225, Hüthig & Wepf Verlag, Basel, Heidelberg, New York 1992). A limiting factor with these polymer systems is however the high water sensitivity of the isocyanate component. In addition, for a sufficiently rapid curing, toxic catalysts, such as e.g. organotin compounds, are necessary.

Known from U.S. Pat. Nos. 4,408,018 and 5,017,649 are polymers with acetoacetate or acrylate groups which can be crosslinked by Michael reaction with di- or polyfunctional acrylates and acetoacetates, respectively. These polymers are, however, not intended as dental materials, but merely as coating compositions.

According to R. J. Clemens, F. Del Rector, J. Coating Techn. 61, 83 (1989) such crosslinked polymers can be used as paints which however showed only a slight resistance to hydrolysis. The accepted reason for this disadvantage is that the amidine base used catalyses the hydrolysis of the crosslinked film in the finished coating.

Finally, it is known from D. L. Trumbo, Polymer Bull. 26, 265 (1991) that even with reaction times of more than 24 hours, various bisacetoacetates, such as 1,3- or 1,4-bisacetoacetoxy methyl benzene or 2,2-dimethyl-1,3-bis(acetoacetyl)-propanediol react with tripropylene glycol diacrylate to give polymers with an average molecular weight of only 2,500 to 15,000 at most.

It is the object of the invention to make available the use of compositions as dental material or constituent of dental material which can be thermally cured at low temperature and within a short period, which are characterized by a good resistance to hydrolysis and a small volume shrinkage on curing, and to provide moulded dental articles which are characterized in particular by resistance to hydrolysis and high hardness.

This object is achieved by the use according to claims 1 to 13 and by the moulded dental article according to claims 14 and 15.

The use according to the invention of a thermally curable composition as dental material or constituent of a dental material is characterized in that the composition contains (a) one or more β-dicarbonyl compounds of formula I as Michael donor,

in which $R^1$ represents a β-dicarbonyl function of formula Ia

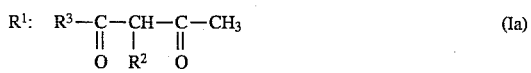

$R^2$ means hydrogen, alkyl or aryl, $R^3$ is oxygen or NH or is not present, Y and X are alkylene, phenylene or alkylphenylene radicals which can be interrupted by oxygen atoms, sulphur atoms or NH groups, Z means alkylene or phenylene and n is an integer in the range from 0 to 15, and (b) one or more α,β-unsaturated carboxylic acid esters of formula II as Michael acceptor

in which $R^4$ is an acrylate group of formula IIa

Y, X and Z are as defined above and $R^5$ is hydrogen, a cyano or an alkyl group and m is an integer in the range from 0 to 15, and the composition can be cured in the presence of a catalyst base (c), the average functionality of the mixture comprising the Michael donors (a) and the Michael acceptors (b) being greater than 2.

Alkyl and alkylene are preferably understood to be those groups which contain 1 to 25, particularly preferably 1 to 10 and quite particularly preferably 1 to 4 carbon atoms and optionally also one or more substituents, such as e.g. halogen atoms, nitro groups or alkoxy radicals. Aryl means radicals which in particular have 6 to 14 carbon atoms and which can be substituted as stated above.

The individual radicals $R^1$, $R^2$, $R^3$, $R^4$, $R^5$, X, Y and Z can in each case be the same or different. Thus, it is e.g. possible that an α,β-unsaturated carboxylic acid ester with different acrylate groups $R^4$ is used. The β-dicarbonyl compounds of formula I preferably usable as Michael donor (a) are acetoacetates and in particular those acetoacetates which have 3 or 4 acetoacetoxy groups in which $R^2$ is hydrogen. These acetoacetates can be prepared from the corresponding di- or polyols by reacting with diketene (cf. R. J. Clemens, Chem. Rev. 86, 241 (1986)) and the diketene-acetone-adduct 2,2,6-trimethyl-1,3-dioxin-4H-one (cf. R. J. Clemens, J. A. Hyatt, J. Org. Chem. 50, 2431 (1985), respectively, or by transesterification with tert. butylacetoacetate (cf. J. C. Gilbert, T. A. Kelly, J. Org. Chem. 53, 449 (1988).

Particularly preferred Michael donors (a) are alkanediol-bisacetoacetates, especially ethylene glycol-1,2- or hexanediol-1,6-bisacetoacetate, oxyalkylenediol bisacetoacetates, in particular triethylene glycol bisacetoacetate or polyethylene glycol-600-bisacetoacetate, and 1,4-cyclohexanedimethanol bisacetoacetate, glycerol trisacetoacetate and pentaerythritol tetrakis-acetoacetate. The α,β-unsaturated carboxylic acid esters of formula II usable as Michael acceptors (b) are either commercial products or can be obtained by esterification of the corresponding di- or polyols with acrylic acid chloride or anhydride. Preferably used as Michael acceptors (b) are acrylic acid esters in which $R^5$ is hydrogen, and in particular those which have 3 or 4 acrylate groups. Quite particularly preferred Michael acceptors are ethylene glycol diacrylate, hexanediol acrylate, tripropylene glycol diacrylate, ethoxylated bisphenol-A-diacrylate, polyethylene glycol-200-diacrylate, trimethylol propane triacrylate and pentaerythritol tetraacrylate.

The mixture consisting of the Michael donors and the Michael acceptors is selected in such a way that its average functionality is greater than two. For the case of a mixture consisting of one Michael donor and one Michael acceptor compound, the average functionality $F_m$ is given by the following equation:

$$F_m = ((a_{MDG} \cdot n_{MD}) + (a_{AG} \cdot n_{MA}))/(n_{MD} + n_{MA})$$

$a_{MDG}$=number of abstractable H atoms in one Michael donor molecule;

$N_{MD}$=number of moles of Michael donor;

$a_{AG}$=number of acrylate groups in one Michael acceptor molecule;

$n_{MA}$=number of moles of Michael acceptor.

The term "abstractable H atoms" means those hydrogen atoms which are directly bound to the carbon atom of the group $R^1$ which is positioned between the two carbonyl groups.

The mixture of Michael donors and acceptors is preferably to be prepared such that n +m ≠O. This means that at least a certain proportion of either β-dicarbonyl compounds with more than two β-dicarbonyl functions $R^1$ or a certain proportion of α,β-unsaturated carboxylic acid esters with more than two acrylate groups $R^4$ is also present.

The compositions used according to the invention are preferably cured in the presence of a catalyst base which is expediently added to a premix consisting of the selected Michael donors and the Michael acceptors shortly before the practical use as dental material. It effects catalysis of the Michael reaction between the Michael donor and the Michael acceptor. Because of the Michael reaction which takes place, there occurs a curing of the composition used according to the invention which leads to solid polymers within a short time even at low temperatures in the range from preferably 15 to 80° C. and particularly preferably 20 to 50° C. This result is surprisingly also achieved if, in a preferred embodiment, the composition is cured in the absence of solvents which are disadvantageous because of a possible health damaging effect.

Used as catalyst base (c) are preferably alkali metal alkoxides, tetraalkyl hydroxides, bicyclic amidines and guanidines. Particularly preferred catalysts are given in the examples. The mixture consisting of the β-dicarbonyl compounds (a) and the α,β-unsaturated carboxylic acid esters (b) is selected such that the molar ratio of (a)/(b) is preferably 0.01 to 20 and particularly preferably 0.1 to 8.0.

In another preferred embodiment, the composition is to be prepared such that, relative to the Michael donor (a), a stoichiometric excess of Michael acceptor (b) is used. The curing of such compositions leads to polymer materials which, after the Michael reaction has finished, still contain unreacted acrylate groups $R^5$ which can be radically polymerised in a 2nd stage. Such materials are preferably used as reactive fillers of dental materials or as polymer matrices of filling materials or dental cements.

In another preferred embodiment, the composition used according to the invention can also contain a modifying agent (d) which has at least one radically polymerisable group whose reactivity vis-à-vis the Michael donor (a) is lower than that of the acrylate groups $R^4$ of the Michael acceptor (b). A content of modifying agent likewise leads to compositions which can be cured in two stages. Thus, the reaction of the Michael acceptors with the Michael donors in the presence of the catalyst base leads to a noticeable viscosity increase of the mixture or to the formation of a more or less solid gel. Curing to give a solid material can then be carried out in a second stage by radical polymerisation. Suitable for such two-stage curing compositions are mixtures of tris or tetrakis acetoacetates together with tri- or tetraacrylates to which mono- or multimethacrylates are added as modifying agents (d). Compared with tri- or tetraacrylates, the latter show a noticeably lower reactivity in a Michael reaction with CH acid compounds, such as acetoacetates, β-diketones or malonic esters. On the other hand, however, they can be radically polymerised ery well. Materials which can be cured in two stages offer e.g. the advantage that the materials can be shaped or excesses removed more easily after the first curing stage when they have a low hardness.

In the case of particularly preferred two-stage-curing compositions, glycerol trisacetoacetate or pentaerythritol tetrakisacetoacetate are used as Michael donors (a), trimethylol propane triacrylate or pentaerythritol tetraacrylate as Michael donors (b), and methyl methacrylate, butyl methacrylate, 2-hydroxyethyl methacrylate (HEMA), 3-methacryloxypropyl-trimethoxy silane, triethylene glycol dimethacrylate, bisphenol-A-glycidyl methacrylate, the urethane dimethacrylate obtained from 2,2,4-trimethyl hexamethylene diisocyanate and HEMA, trimethylol propane trimethacrylate or pentaerythritol tetramethacrylate as modifying agents (d). When using dimethacrylates or multimethacrylates, so-called interpenetration networks (IPN) form, which impart an excellent hardness and strength to the cured compositions. Finally, methacrylates with acetoacetoxy groups, such as in particular 2-acetoacetoxyethyl methacrylate (AAEMA) can also preferably be used as modifying agents. By using such modifying agents, compositions with high hardness can be obtained.

If functionalisation of the cured compositions is desired, monomeric acetoacetates or acrylates with non-acidic functional groups, such as e.g. amino-, hydroxy-, nitro- or halogen groups, or acrylonitrile- or vinyl ketone derivatives can be added to them prior to the curing reaction. Cured compositions containing free OH- or epoxy groups can e.g. be obtained by reacting a mixture of pentaerythritol tetrakisacetoacetate and trimethylol propane triacrylate with 2-hydroxyethyl acrylate or glycidyl acrylate.

The compositions used according to the invention can be reinforced with organic or inorganic particulate fillers or fibres, as a result of which composite materials are produced. Suitable as fillers are in particular precipitated or pyrogenic silicas, calcium carbonate and calcium hydroxide, glass fillers or X-ray opaque substances, such as e.g. ytterbium fluoride, barium sulphide and barium hydroxide. Preferred as fibres are short or long glass fibres and cellulose or polyamide fibres. Improved adhesion or binding-in of the fillers into the Michael polymer matrix can be achieved by silanisation with acryloxyalkyl silanes, such as e.g. 3-acryloxypropyl trimethoxysilane which can be purchased. The compositions can also contain usual auxiliaries and additives, such as e.g. dyes, pigments, thixotropic auxiliaries, stabilisers, flavours or microbicidally active ingredients.

The compositions used according to the invention are characterized by a combination of properties which have a particular significance for dental materials. For example, they show only slight sensitivity to water which manifests itself in only a slight change in the mechanical properties during storage in water for several days. The compositions can also be varied through the choice of the Michael donors and Michael acceptors used in such a way that cured materials having mechanical properties ranging from hard and brittle to soft and elastic are obtained.

If the compositions are used as unmoulded materials, then preferred dental materials are filling composites, dental adhesives, fixing cements or impression materials. In contrast, the compositions can also produce moulded dental articles which comprise the cured composition. These dental articles are preferably used in the replacement or restoration of teeth, i.e. of natural or artificial teeth. They preferably exist in the form of an artificial tooth, an inlay, an onlay, a crown, a prosthesis or a section of a prosthesis.

On using the compositions for binding substrates to natural or artificial teeth or to prostheses, the compositions are applied on the selected area of the tooth or prosthesis, the substrate is brought into contact with the applied composition and the compositions are cured.

If the compositions are to be used as impression materials, they are applied and cured on the area of a natural or artificial tooth or denture which is to be modelled.

When using the composition for the restoration or replacement of natural or artificial teeth, the composition (a) is shaped in the desired way, (b) arranged in the selected area of the tooth or denture and (c) cured. The process stage (c) can also be conducted between the stages (a) and (b).

The invention is explained in more detail below with reference to examples.

EXAMPLES

The following compounds are used in the examples below.

Michael donors (a): hexanediol-1,6-bisacetoacetate (HDDAA), polyethylene glycol-600-bisacetoacetate (PEG-600-DAA) glycerol trisacetoacetate (GTAA), pentaerythritol tetrakisacetoacetate (PETAA);

Michael acceptors (b): hexanediol-1,6-diacrylate (HDDA), polyethylene glycol-400-diacrylate (PEG-400-DA), trimethylol propane triacrylate (TMPTA), pentaerythritol tetraacrylate (PETA);

Modifying agents: methyl methacrylate (MMA), triethylene glycol dimethacrylate (TEGDMA), 2-acetoacetoxyethyl methacrylate (AAEMA);

Catalyst bases: diazabicyclo (4,3,0) nonene (DBN), diazabicyclo (5,4,0) undecene (DBU), tetrmnethylguanidine (TMG);

Photoinitiators: mixture of camphor quinone (CC) and N-(2-cyanomethyl)-N-methylaniline (CEMA);

Fillers: barium glass (BAG), ytterbium fluoride ($YbF_3$), highly dispersed silica (Ox 50 or Aerosil 200); $SiO_2$-$ZrO_2$ mixed oxide (Sphärosil).

Example 1

Preparation of solid dental materials

Compositions comprising different acrylates and acetoacetates were prepared and mixed with 2.0 mol. % DBN —relative to the quantity of acetoacetate used. The working time of the mixtures and selected properties of the cured compositions are given in

TABLE 1

| Acrylate/acetoacetate | HDDA/ PETAA | TMPTA/ PETAA | PETA/ GTAA |
| --- | --- | --- | --- |
| working time (min) | 7 | 2 | 1.5 |
| Shore-D hardness | 52 ± 1 | 64 ± 3 | 83 ± 2 |
| Bending strength (MPa) | nd | 62.1 | 73.2 |
| E-modulus (MPa) | nd | 1960 | 2200 |
| Water absorption (7d, %) | nd | 5.5 | 5.8 |
| Water solubility (%) | nd | 1.1 | 0.6 | nd = not determined

The parameters given above were determined according to the ISO Standard 4049.

The uncured compositions can be used as dental adhesives or as matrix polymers of dental adhesives and fixing cements.

Example 2

Preparation of soft impression materials

Combinations of different functionalised acrylates and the bisacetoacetates PEG-600-DAA and HDDAA were prepared and reacted at room temperature. The molar ratio of the acrylate and acetoacetate groups was 1:1 and 2.0 mol. % DBN were used as catalyst base. The working time (WT) of the mixtures and the Shore-A hardness of the cured materials are given in Table 2:

TABLE 2

| Acrylate | PEG-600-DAA WT(min)/Shore-A hardness | HDDAA WT(min)/Shore-A hardness |
| --- | --- | --- |
| PEG-400-DA | 8/31 ± 1 | 3/38 ± 1 |
| HDDA | 6/30 ± 1 | 4/39 ± 1 |
| TMPTA | 2/52 ± 3 | 1/66 ± 1 |
| PETA | 0.5/67 ± 3 | 0.8/74 ± 2 |

It is shown that the Shore-A hardness of the materials can be controlled by the functionality of the acrylate component. The hardness increases with increasing functionality.

Moreover, the soft materials can be further strengthened by use of fillers, which can be seen from the example of two PEG-600-DAA materials (A and B).

TABLE 3

| Composition (wt. %): | A | B |
| --- | --- | --- |
| PEG-600-DAA | 62.5 | 64.2 |
| PETA | — | 22.5 |
| TMPTA | 24.4 | — |
| DBN | 0.6 | 0.4 |
| Aerosil 200 | 12.5 | 12.5 |
| Shore-A hardness | 79 ± 2 | 82 ± 1 |

Example 3

Composites as filling materials.

Two filling materials with a degree of filling of 60 (material 1) and 76.7 wt. % (material 2) based on a PETAA/PETA mixture and having the following composition were prepared:

TABLE 4

| Component | Material 1 (wt. %) | Material 2 (wt. %) |
| --- | --- | --- |
| PETAA | 22.6 | 14.4 |
| PETA | 16.8 | 8.5 |
| OX 50 | 41.3 | — |
| $YbF_3$ | 18.7 | 17.1 |
| BaG | — | 43.1 |
| Sphärosil | — | 16.5 |
| DBN | 0.6 | 0.4 |

After curing the materils at room temperature (30 min) and 3 hours' storage at 50° C., the following properties were determined:

TABLE 5

| Property | Material 1 | Material 2 |
| --- | --- | --- |
| Volume shrinkage (%) | 2.2 | 1.8 |
| Bending strength (MPa) | 24.1 | 43.8 |
| Bending-E-modulus (MPa) | 2300 | 7100 |
| Water absorption (%) | nd | 2.7 | nd = not determined.

Material 2 can also be used in advantageous manner for producing moulded dental articles.

Example 4

Two-stage-curing compositions for filling materials and dental cements a) Composition based oil an acrylate-acetoacetate/methacrylate mixture A mixture comprising the following components was formed:

28.4 wt. % PETAA
21.2 wt. % PETA
49.5 wt. % TEGDMA
0.1 wt. % CC
0.2 wt. % CEMA and
0.6 wt. % DBN.

The PETA was added at the end. With the mixture, various testpieces were manufactured, the working time of the mixture being 10 minutes. The Michael reaction carried out at room temperature ultimately gave a material with a Shore-A hardness of 85±4. Through further light polymerisation (3 minutes, Spectramat - standard commercial blue light lamp, manufacturer: IVOCLAR AG, Liechtenstein), the material became noticeably harder which is manifested in a Shore-D hardness of 75±4, a bending strength of 57.4 MPa and a bending-E-modulus of 1420 MPa.

b) Composition based on an acrylate-acetoacetate mixture with an acrylate excess:

With compositions based on PETAA mixtures with different PETA content, the Shore hardness was investigated after the 1st curing stage (Michael reaction) and after the 2nd curing stage (3 minutes' light polymerisation in the Spectramat):

TABLE 6

| | Mol acetoacetate/mol acrylate | | | |
| --- | --- | --- | --- | --- |
| Composition (wt. %) | 1:5 | 1:6 | 1:8 | 1:10 |
| PETAA | 20.9 | 18.1 | 14.2 | 11.7 |
| PETA | 77.9 | 80.7 | 84.7 | 87.3 |
| DBN | 0.4 | 0.4 | 0.3 | 0.2 |
| CEMA | 0.5 | 0.5 | 0.5 | 0.5 |
| CC | 0.3 | 0.3 | 0.3 | 0.3 |
| 1st stage: Shore hardness | 49 D | 90 A | 73 A | 63 A |
| 2nd stage: Shore hardness | 72 D | 83 D | 83 D | 84 D |

It can be seen that the hardness after the 1st stage depends on the acrylate excess and that in all examples the strength of the materials can be clearly increased by the light polymerisation.

Bending tests were carried out with filled and unfilled materials based on PETAA/PETA mixtures (molar ratio 1:5). The results shown in Table 7 prove that the mechanical properties are only slightly impaired after water storage. Consequently, compositions which contain an excess of Michael acceptor are preferred if a very low water sensitivity is required.

TABLE 7

| Property | Unfilled material | Composite material[a] |
| --- | --- | --- |
| Bending strength (MPa) | 64.2 | 70.5 |
| after 24h storage in water | 56.3 | 59.1 |
| bending-E-modulus (MPa) | 1800 | 5900 |
| after 24h storage in water | 1900 | 5900 |

[a] Composition (wt.%):PETAA:8.4;PETA:31.2;DBN:0.2;Ox50:41.2;$YbF_3$: 18.7; CC: 0.1; CEMA: 0.2.

The above composite material can also be used in advantageous manner for the production of dental articles.

If modifying agents which, in addition to the radically polymerisable groups, also have groups which can be bound covalently into the polymer network are added to the compositions according to the invention, then particularly preferred compositions result. Example 5 shows this.

Example 5

Preparation of functionalised dental materials or dental fillers a) 0.1 mol PETA are added to a mixture of 0.1 mol AAEMA, 0.1 mol GTAA, 0.2 mol. % DBU (relative to GTAA) and 0.3 wt. % CEMA (relative to the total mass). After 25 min. at room temperature and a further 3 hours' storage at 50° C., a material with a Shore-A hardness of 87 is obtained. After exposure to light in the Spectramat (3 minutes), the hardness increases to 74 Shore-D.

b) 0.1 mol PETA are added to a mixture of 0.1 mol acetoacetic acid methyl ester, 0.1 mol GTAA, 0.2 mol. % DBU (relative to GTAA) as well as 0.2 wt. % CC and 0.5 wt. % CEMA (relative to the total mass). After 25 min. at room temperature and a further 3 hours' storage at 50° C., a material with a Shore-A hardness of 82 is obtained. After exposure to light in the Spectramat (3 minutes), the hardness scarcely increases (84 Shore-A).

c) 5 mmol PETA and 50 w-t.% MMA (relative to the total mass) are added to a mixture of 5 mmol PETAA, 0.2 mol. % DBU (relative to PETAA) as well as 0.3 wt. % CC and 0.5 wt. % CEMA (relative to the total mass). After 25 minutes at room temperature and a further 3 hours' storage at 50° C., a material with a Shore-A hardness of 53 is obtained. After exposure to light in the Spectramat (3 minutes), the hardness scarcely increases (54 Shore-A).

Comparison of experiment (a) with experiments (b) and (c) shows that through the reaction of AAEMA with the GTAA/PETA mixture a functionalised Michael polymer network is formed which carries polymerisable methacrylate groups. In contrast to the monofunctional MMA which is only bound physically in Experiment (c), the formed polyfunctional Michael resin methacrylate from (a) can be further strengthened very well by light polymerisation. Experiment (b) proves that the 2nd curing stage does not take place because of the polymerisation of non-reacted acrylate component, Functionalised dental materials or fillers of dental materials can also be prepared in analogous manner with other functionalised acrylate or acetoacetate components, The compositions described in this example can be used e,g, as dental adhesives or in a filled form as fixing cements or filling composites.

We claim:

1. A thermally curable composition suitable for use as or in a dental material comprising:

(a) one or more β-dicarbonyl compounds of formula I as a Michael donor

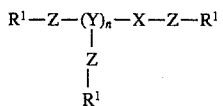  (I)

Wherein $R^1$ is a β-dicarbonyl group of formula Ia

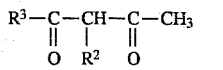  (Ia)

$R^2$ is hydrogen, alkyl or aryl; $R^3$ is oxygen, NH or not present, Y and X are alkylene, phenylene or alkylphenylene radicals which can be interrupted by oxygen atoms, sulfur atoms or NH groups, Z is alkylene or phenylene, n is an integer in the range from 0 to 15;

(b) one or more β-unsaturated carboxylic acid esters of formula II as a Michael acceptor

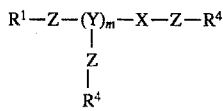  (II)

Wherein $R^4$ is an acrylate group of formula IIa;

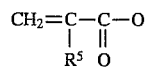  (IIa)

Y and X are alkylene, phenylene or alkylphenylene radicals which can be interrupted by oxygen atoms, sulfur atoms or NH groups, Z is alkylene or phenylene, $R^5$ is hydrogen, a cyano or alkyl group, m is an integer in the range from 0 to 15;

(c) a catalyst base; and (d) a modifying agent having at least one radically polymerizable group, wherein said composition is capable of undergoing a first curing step mediated by said catalyst base and a second curing step involving said modifying agent.

2. The composition according to claim 1, wherein the sum of n plus m is not equal to zero.

3. The composition according to claim 1 wherein said composition is capable of being cured in the absence of solvent.

4. The composition according to claim 1, wherein said Michael donor comprises acetoacetates with three or four acetoacetoxy groups and $R^2$ is hydrogen.

5. The composition according to claim 1 wherein said Michael acceptor comprises acrylic acid esters with three or four acrylate groups, and $R^5$ is hydrogen.

6. The composition according to claim 1, wherein said composition comprises a stoichiometric excess of said Michael acceptor relative to said Michael donor.

7. The composition according to claim 1, wherein said modifying agent has a reactivity relative to said Michael donor lower than that of the acrylate groups $R^4$ of said Michael acceptor.

8. The composition according to claim 1, wherein said composition is a dental filler material.

9. The composition according to claim 1, wherein said composition is a dental filling composite material.

10. The composition according to claim 1, wherein said composition is in cured form.

11. The composition according to claim 1, wherein said dental meterial comprises an artificial tooth, an inlay, an onlay or a crown.

12. The composition according to claim 1, wherein said dental composition is a dental adhesive.

13. The composition according to claim 1, wherein said dental composition is a dental fixing cement.

14. The composition according to claim 1, wherein said dental composition is a dental impression material.

15. The composition according to claim 1, wherein said Michael donors and said Michael acceptors have an average functionality of greater than 2.

16. The compostion according to claim 1, wherein said modifying agent is a methacrylate.

17. A thermally curable composition suitable for use as or in a dental material comprising:

(a) one or more β-dicarbonyl compounds of formula I as a Michael donor

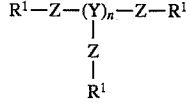  (I)